US005776778A

United States Patent [19]
Kajander et al.

[11] Patent Number: 5,776,778
[45] Date of Patent: Jul. 7, 1998

[54] GROWTH FACTOR PREPARATION OF THYMOCYTE CELL CULTURE MEDIUM ITS PRODUCTION AND USE

[76] Inventors: Olavi Kajander, FIN-71310, Vehmersalmi; Ilpo Kuronen, Lataajanpolku 1F 43, FIN070460 Kuopio; Kaarina Tikkanen, Maaherrankatu 35 as 9, FIN-70100 Kuopio, all of Finland

[21] Appl. No.: 762,830

[22] Filed: Dec. 10, 1996

[30] Foreign Application Priority Data

Jun. 10, 1994 [FI] Finland ................................. 942773

[51] Int. Cl.⁶ .............................. C12N 5/02; C12N 5/06; C12N 5/08; C07K 14/475
[52] U.S. Cl. .................. 435/405; 435/384; 435/326; 435/352; 435/353; 435/354; 435/355; 435/372.2; 435/372.3; 530/399; 530/351; 530/300; 530/387.1; 436/547
[58] Field of Search ..................... 530/399, 351, 530/300, 387.1; 424/578, 579, 580; 435/326, 352, 353, 354, 355, 366, 372.3, 384, 405; 436/547

[56] References Cited

U.S. PATENT DOCUMENTS 4,613,459  9/1986  Cantor et al. ............................ 530/351

FOREIGN PATENT DOCUMENTS 310 056   4/1989  European Pat. Off. .
2 170 818 8/1986  United Kingdom .

OTHER PUBLICATIONS

Sredni et al., Induction of B lympohcyte colony growth in vitro by thymus-derived stimulating factor, Eur. J. Immunol., 8:681–685, 1978.

Andersson et al., Clonal growth and maturation to immunoglobulin secretion in vitro of every growth–inducible B lymphocyte, Cell, 10:27–34, Jan. 1977.

Ganong et al., Review of Medical Physiology, Appleton and Lange (Norwalk, CT), p. 483, 1995.

Roitt, I, "The Acquired Immune Response, I–Consequences of Antigen Recognition", Essential Immunology Chpt. 6, 7th ed., 1991, pp. 105–128.

Roitt, I. "The Acquired Immune Response, II Production of Effectors", Essential Immunology, chpt 7, 7th Ed., 1991, pp. 129–151.

Robert E. Hawkins, "Cell selection strategies for making antibodies from variable gene libraries: trapping the memory pool", Eur. J. Immounol., 1992, 22, pp. 867–870.

Borrebaeck et al. "In Vitro Immunization. Effect of Growth and Differentiation Factors on Antigen–Specific . . . ", The Journal of Immunology, May 15, 1986, pp. 3710–3715.

Kwekkeboom et al, "An efficient procedure for the generation of human monoclonal . . . ", Journal of Immunological Methods, 160(1993) pp. 117–127.

*Primary Examiner*—Stephen Walsh
*Assistant Examiner*—Claire M. Kaufman
*Attorney, Agent, or Firm*—Cushman Darby & Cushman IP Group of Pillsbury Madison & Sutro LLP

[57] ABSTRACT

The present invention relates to a growth factor preparation derived from a mixed lymphocyte culture, and a process for its production. The invention also relates to a cell culture medium containing said growth factor preparation. The invention further relates to a process for culturing plasma cells and producing antibodies by using said cell culture medium.

12 Claims, No Drawings

5,776,778

1

GROWTH FACTOR PREPARATION OF THYMOCYTE CELL CULTURE MEDIUM ITS PRODUCTION AND USE

This is a Continuation of: International Appln. No. PCT/FI95/00335 filed Jun. 9, 1995 which designated the U.S.

FIELD OF THE INVENTION

The present invention relates to a growth factor preparation derived from a mixed lymphocyte culture, and a process for its production. The invention also relates to a cell culture medium containing said growth factor preparation. The invention further relates to a process for culturing plasma cells and producing antibodies by using said cell culture medium.

BACKGROUND OF THE INVENTION

When a foreign substance, i.e. an antigen, enters the system of an animal, it raises an immune response therein, said immune response being caused by cells called lymphocytes. There are two main types of lymphocytes, i.e. T lymphocytes and B lymphocytes. They are also referred to as T cells and B cells, respectively. T cells are responsible for cell-mediated immunity and B cells for the production of antibodies.

Polyclonal antibodies are conventionally produced by immunizing an animal with an antigen and isolating the produced antibodies therefrom. When B cells encounter their antigen, they are activated, proliferate, and finally differentiate to become entirely differentiated antibody-producing plasma cells. This is a multi-phase series of events, in which participate a number of activators, for instance interleukins (IL) and interferon gamma (IFN gamma). Furthermore, the differentiation of B lymphocytes into antibody-forming plasma cells usually also requires the presence of T lymphocytes.

To facilitate the production of antibodies, attempts have also been made to culture B cells in vitro, but the difficulties have been considerable since B lymphocytes usually soon die under these conditions. Only malignant lymphocytes may grow. The inventing of the hybridoma technique marked a revolutionary development in the field. It was learnt to fuse an antibody-producing lymphocyte with a myeloma cell, whereby an antibody-producing, immortal hybridoma was obtained, said hybridoma producing only one type of antibody, i.e. a monoclonal antibody. Normally, it is necessary to prepare a number of hybridomas, which are first screened and from among which are then selected the ones with the desired antigen-specificity. In other words, in a large initial amount of cells only few have the desired properties.

Another possible way of producing antibodies in vitro has been the use of transformed B lymphocytes. The efficiency of the transformation has, however, been extremely low, and the antibody production has been scanty and unstable. It has later been possible to increase stability by fusing transformed B lymphocytes with myeloma cells.

The isolation of antibody-coding gene sequences and the expression entirely or partly thereof in microbe vectors have been recently successful from both a murine and human lymphocyte material by means of the PCR technique. The number of genes for different antibodies is enormous, and in the production of a library, light and heavy-chain genes are further randomly combined. Consequently, the transfer of the genes of a specific polyclonal antibody is still only aimed

2 at. By first enriching a cell population it is possible to increase the number of desired gene copies (Hawkins, R. and Winter, G. 1992, Eur. J. Immunol., 22, 867–870). The enrichment was carried out by "capturing" cells by means of an antigen.

As early as over ten years ago, T lymphocytes were successfully cultured almost without restrictions in a test tube by means of growth factor IL-2, which enables for instance cancer immunotherapy, wherein tumor-specific killer T cells are collected from a patient, said cells being cultured in vitro and then activated and reintroduced into the patient to kill the tumor. On the other hand, the cultivation of B lymphocytes and the production of antibodies in vitro without transformants or hybridomas have not been successful so far. In order to grow, B lymphocytes require many types of growth factors, of which at least part is still unknown. Accordingly, attempts have been made to culture B lymphocytes by adding growth factors of different types to a conventional cell culture medium.

It is known that the activation of B cells starts when an antigen presenting cell encounters an antigen recognizing B cell, said B cell activating in the presence of IL-4 and IL-1, whereby receptors for IL-2 and other interleukins are produced in the cell. IL-2, IL-4 and IL-5 (in mouse) drive cell division and then differentiate into entirely differentiated antibody-forming plasma cells in the presence of IL-4, IL-5, IL-6 (in man) and IFN gamma. T cells also participate in this series of events (Roitt, I. Essential Immunology, 7th edition, Blackwell Scientific Publications, London, 1991). IL-6, connected with the maturation of a B lymphocyte, is also referred to as a plasma cell growth factor. The term is however misleading, because IL-6 does not grow entirely matured plasma cells in a culture so that they would multiply, form a long-term culture and produce their antibody in a test tube.

In quest of the most promising results, a growth factor preparation suitable for B lymphocytes has been obtained by using so-called mixed lymphocyte cultures (MLC), wherein different lymphocytes are cultured together. After the cultivation, these lymphocytes are removed, and the supernatant is used as a growth factor preparation, which is added to a conventional cell culture medium as a supplement for the desired B lymphocytes.

Borrebaeck, C. and Möller, S., 1986, J. Immunol. 136, 3710–3715, have managed to raise an immune response in a spleen culture by using a culture medium, which contained, in addition to the conventional ingredients, a cell-free supernatant derived from an MLC of two different mouse strains and a phorbol myristate acetate (PMA) stimulated mouse EL-4 thymus cell culture. The mouse B lymphocytes grown in this medium did not, however, survive long, but the optimum antigen stimulation was reached in about 5 days, after which it declined again. After having reached their optimum stimulation, the B lymphocytes were maintained by fusing them into hybridoma cells, which then produced the desired monoclonal antibody.

Kwekkeboom, J. et al., 1993, J. Immunol. Methods 160, 117–127, have prepared human monoclonal antibodies by activating B lymphocytes used for hybridization first in vitro with mouse thymoma EL4B5 cells in the presence of a human T cell supernatant. The B lymphocytes were cultured in a medium containing irradiated EL4B5 cells, T cell supernatant, and possibly PMA, the B cells thus both multiplying and differentiating to produce antibody. The stimulation was strong but lasted for a short period. The peak was reached within 5–8 days, but after 15 days the growth of the cells ceased entirely. Those B lymphocytes which produced the desired antibody were screened and used to produce hybridomas. It was noticed that the fusion efficiency of the stimulated B cells taken from the peak stage was multiple in comparison with the use of unstimulated B lymphocytes.

SUMMARY OF THE INVENTION

Surprisingly, a growth factor preparation has now been invented, which enables long-term culture of B lymphocytes and efficient antibody production even without producing a hybridoma or other transformation. The growth factor preparation of the invention is characterized in that it is derived from a mixed thymocyte culture, said thymocytes originating from different species of mammals. It preferably consists of the supernatant of said mixed thymocyte culture of different species of mammals. The cell culture medium of the invention is characterized in that it contains the growth factor preparation derived from a mixed thymocyte culture, said thymocytes originating from different species of mammals. The invention further relates to a process for the production of said growth factor preparation, characterized in that thymocytes originating from different species of mammals are co-cultured in a cell culture medium, whereafter the cells are removed and the conditioned medium is recovered. The medium of the invention can be used in a process for culturing plasma cells and for producing antibodies. In this context, plasma cells also include transformed B lymphocytes, for instance B lymphocytes transformed with the Epstein-Barr virus or cells transformed into hybridomas. These processes are also included within the scope of the invention, and they are characterized by what is disclosed in claims 8 and 10. The preferred embodiments of the invention are disclosed in the dependent claims.

By means of the preparation of the invention, it is possible, for the first time, to efficiently produce polyclonal antigen-specific antibodies in a culture by directly using spleen cells of an immunized animal or another source of lymphocytes thereof, such as a lymph node, peripheral blood or tissue. These antibody-producing, differentiated B lymphocytes can now be cultured on a long-term basis. The process of the invention also makes it possible to clone a selected monospecific antibody from a polyclonal response.

The growth factor preparation of the invention differs in its effect from the known growth factors firstly in that it is very specific, that is, it stimulates the antibody production of a differentiated antigen-activated B lymphocyte, i.e. a differentiated plasma cell. With the interleukin and other growth factor preparations known to date, for instance, it has been possible to stimulate non-differentiated lymphocytes to grow, produce antibodies and differentiate, but long-term culture or cloning has not been possible. The growth-stimulating effect of the preparation of the invention differs from the known interleukins such as IL 2, 3, 4, 5 and 6 affecting B lymphocytes, but its more specific nature is not known yet. Lymphocyte mitogens usually also stimulate T cells to grow, but the preparation of the invention does not do so. However, the preparation of the invention also stimulates the growth and antibody production of transformed B lymphocytes, hybridomas included. This is a second aspect of the present invention.

The growth factor preparation of the invention further differs from prior art growth factor preparations based on mixed cultures in that it is produced from a mixed thymocyte culture, wherein the thymocytes originate from different species. Previously, only intra-species thymocyte culture has been used to produce a preparation wherein the cells concerned cannot be propagated on a long-term basis. According to the present invention, cultures can be split and maintained for a month or longer. Previously, the cells died within about a week.

DETAILED DESCRIPTION OF THE INVENTION

The growth factor preparation of the invention can be produced by co-incubating thymocytes derived from different animal species. If thymocytes are taken from one animal only or from different strains of the same animal species, the desired B lymphocyte stimulation effect is not achieved. The thymocytes are preferably obtained from the thymus of the animal, but other T cell tissue, such as a spleen, can also be used. The thymuses are aseptically removed, and the thymocytes are mechanically released, washed and then inoculated into a conventional cell culture medium so as to have a high cell density, for instance at least about $10^6$ cells/ml, usually about $10^6$–$10^8$ cells/ml, typically about $10^7$ cells/ml. Said cell culture medium consists of a conventional basic cell culture medium, such as DMEM or RPMI 1640 or the like, to which have been added conventional additives, such as an antibiotic and supplement, such as fetal calf serum (FCS) or the like, such as colostrum preparation Viable (Valio Bioproducts, Finland), or even other serum-free substrates, such as a defined synthetic hybridoma substrate from Gibco (cat. no. 10123-024, Gibco, Paisley, Scotland). Different types of basic cell culture media are commercially available, of which for instance RPMI 1640 and DMEM (Gibco) can be mentioned in this context. An RPMI-based HMIX medium is preferably used in the present case, the composition of which medium is disclosed in the working examples.

The thymocytes are preferably obtained from mice and rats. The cells have a different MHC (major histocompatibility complex) on their surface, and they recognize one another as foreign, whereby they start a tissue rejection reaction, i.e. a rejection. As a result of this activation, the T cells produce the new growth factor or factors required for maintaining the stimulation of the B cells. The propagation is carried out under normal cell culture conditions: 5–10% by volume of $CO_2$, 90–95% by volume of air, about 37° C., for a few days, usually 1–3 days, particularly 2 days, after which the cells are separated by centrifugating, and the supernatant is filtered, preferably by means of sterile filtration, and recovered. The B lymphocyte-stimulating growth factor preparation obtained in this manner can then be frozen for later use, if desired.

The animal used as a source of B lymphocytes can first be immunized in a conventional manner with a desired antigen, and when the immune response is at its most active, the B lymphocytes are separated therefrom, for instance from peripheral blood with the Ficoll-Paque method (Roitt, I., supra) or from a lymph node, as from spleen cells in a manner known per se. The isolated B lymphocytes are then cultured under normal cell culture conditions and in the cell culture medium described above, further supplemented with about 1–50% by volume, preferably 10–40% by volume and particularly 20–30% by volume of the above-mentioned growth factor preparation. Under these conditions, the differentiated plasma cells survive, proliferate and produce antigen-specific antibody for several weeks, even months, while non-differentiated B lymphocytes die off. The best results have been obtained by using mouse B cells, which have been successfully propagated in producing antibody in such a manner that it has been possible to split the culture even 1:3 once a week for a period of six weeks. Since antibody production is a process quite similar with all mammals, it is also possible to grow for instance human B cells by the process.

The present invention now provides a possibility to maintain the growth of in vivo-stimulated B lymphocytes and the polyclonal stimulation and production of antibody under in vitro conditions without the presence of an antigen by utilizing a growth factor preparation derived from a mixed thymocyte culture, said thymocytes originating from different species of mammals. By this process, it is possible to switch the active antibody production of an animal to a culture and to enrich the in vivo antigen-stimulated, antibody-producing cells.

The production of a specific antibody in a culture without the presence of an antigen is based on a special, new growth factor preparation, which does not stimulate lymphocytes non-specifically. The stimulation thereof is directed to cells which have just undergone a differentiation in an animal as a result of antigen stimulation and become differentiated, antibody-producing cells. The preparation maintains the proliferation and antibody-production of these cells in an in vitro culture. The process thus requires that lymphocytes, such as spleen cells, of an immunized mammal, such as mouse, be used as the starting material. By adding the preparation to a cell culture medium, it is possible to produce polyclonal antibodies in a mouse spleen cell culture, and the production is primarily directed to the antigen or antigens with which the immunization of the animal was carried out.

Synthetic peptides, purified proteins and microbes or separated components thereof have been tested as antigen preparations. In all cases, long-term production of a polyclonal antibody and the proliferation of B lymphocytes in a culture have been obtained. The production of a specific antibody even exceeds the capability of hybridomas to produce an antibody when measured with ELISA technique. The response, as well as the cell proliferation, continues for weeks or months despite the fact that the antigen is not present in the culture. Finally, the culture consists almost 100% of B lymphoblasts, all or most of which apparently secreting an antibody.

The normal, non-antigen-stimulated spleen lymphocytes, which constitute the majority of spleen cells, do not proliferate in a culture and typically die within about a week, so that two weeks after the culture was started, these cells cannot be found any longer. The preparation does not stimulate these cells, and the situation does not significantly differ from one where the preparation has been omitted from a culture. The stimulating effect of the preparation is thus only directed to differentiated, antibody-producing cells which have been stimulated with an antigen in advance.

Another advantage of the growth factor preparation of the invention is that it stimulates in vitro the growth of transformed B lymphocytes, such as hybridomas, and the production of a monoclonal antibody.

By the process of the invention for culturing lymphocytes, it is possible to clone transformed B lymphocytes, hybridomas included. The process of the invention further provides a possibility of cloning antibody-producing, non-transformed cells. Previously, it has not been possible to clone differentiated, antibody-producing B lymphocytes by means of cell culture due to the fact that long-term culture of differentiated B cells has not been possible. Cloning now makes it possible to select from a polyclonal response a cell producing a desired antibody, expand this cell clone, produce the antibody formed by it in a culture and, if desired, isolate the antibody gene or immortalize the cell by the conventional hybridoma technique. In the two last-mentioned cases, only the desired gene or hybridoma producing the desired antibody is obtained, which provides a significant improvement in efficiency in comparison with the production of conventional gene libraries or hybridomas. In such conventional production, desired targets, desired cells and the antibody genes thereof are only few, for instance one in a million. An animal has over a million different B cell clones, each consisting of a varying number of cells. It is thus quite difficult to find a desired gene or to screen an antibody. By the new process, the desired cells can be enriched while the other cells die, and thus the probability of finding the desired cell even in a polyclonal culture highly increases even without cloning.

This provides a possibility of selecting a monospecific antibody by cloning it from a polyclonal response. It is thus possible to produce, without producing a hybridoma or other transformation, a specific—monospecific, if desired—antibody formed by the species concerned. Good myeloma cell lines for the production of hybridomas are only known with mice and rats. The production of monospecific antibodies with other animal species has thus been impossible or at least problematic. The invention also provides possibilities for enriching an antigen-specific plasma cell population by culturing, thus enabling the enrichment of the genetic material regulating the antibody production.

The means provided by the present invention for producing antibodies in culture creates opportunities in research as well as in therapy. By means of the preparation, it is even possible to produce enriched gene libraries of polyclonal antibodies, for instance an anti-albumenpolyclonal library, from which each user may select a monoclonal antibody of desired specificity or to a desired epitope. In principle, a polyclonal antibody is a popular tool both in research and therapy. Polyclonal antibodies can include even a thousand different target-recognizing antibodies, each such antibody naturally having its own cell clone, and each clone having its unique gene sequence.

The following examples describe possible embodiments of the invention. The invention, however, is not limited to the examples given.

EXAMPLE 1

The growth factor preparation was produced by aseptically removing thymuses from one rat (Wistar, Fisher (4-344) or Spraque-Dawley) and from one mouse (Balb/c, B6 or CD2FI). The animals were obtained from the National Laboratory Animal Center, University of Kuopio. The cells were released in a sterile manner by means of needles (18 gauge) or by pressing the thymuses through a screen. The washed thymocytes were suspended in a cell culture medium so as to produce a high cell density, i.e. about $2-4 \times 10^6$ cells/ml. The cell culture medium used was HMIX, which contains RPMI 1640 or DMEM medium (Gibco), L-glutamine 2 mM, natriumpyruvate 1 mM, 2-mercaptoethanol 50 µM, HEPES buffer (Gibco) 10 mM and non-essential amino acids (Gibco) in 1× concentration. 10% of FCS and 100 µg/ml of gentamycin were also added to the HMIX medium. After an incubation of about 48 hours under normal cell culture conditions, the medium was separated by centrifugation, filtered and frozen. The growth factor preparation obtained in this manner was diluted in a cell culture medium for use.

EXAMPLE 2

Mice were immunized in a conventional manner by injecting the antigen intraperitoneally or subcutaneously once in complete Freund's adjuvant and twice in incomplete Freund's adjuvant at intervals of two weeks. The amount of the required pure antigen was about 10 μg in each immunization. Finally, a booster was given i.p. or i.v. 3–5 days before the animal was killed.

The mouse was killed, and the spleen was aseptically removed and transferred to a cold, 4°–8° C., serum-free basic cell culture medium. The spleen was rinsed three times, and the spleen cells were removed to a warm (37° C.) cell culture medium by means of needles (18 gauge) or by pressing the spleen through a screen. The cells were washed and suspended in a cell culture medium containing 10% of FSC, 100 IU/ml of penicillin and 100 μg/ml of streptomycin, the suspension was dispersed into well plates or the cells were cultured in cell culture flasks at a temperature of 37° C. in an incubator with 5% of $CO_2$/95% of air. About $1\times10^8$–$3\times10^8$ lymphocytes were obtained from the immunized spleen.

To produce a polyclonal antibody, the spleen cells were cultured in a commercial RPMI medium (Gibco) or in an RPMI-based medium mixture (HMIX), whereto 10% of FCS and antibiotics had been added to prevent bacterial contamination. The growth factor preparation produced according to Example 1 was added to the cells up to 50% to stimulate antibody production.

To produce monoclonal antibodies, the spleen cells were fused with rapidly multiplying, non-secreting mouse myeloma cells. These cells are generally available at cell banks, for instance P3X63-Ag8.653, which is deposited with ATCC under reference CRL-1580. The cells were cultured for 7 days in the RPMI or HMIX medium (+10% of FCS and 100 μg/ml of gentamycin) under the influence of a hypoxantine-aminopterine-thymidine (Gibco) (HAT) selection, 7 days, whereafter the growth factor preparation produced according to Example 1 was added to stimulate the growth of hybridomas and the antibody production.

EXAMPLE 3

Balb/c mice were immunized according to Example 2 into the peritoneal cavity by using as antigens: test 1) human synthetic osteocalcinpeptide, containing the sequence amino acids 1–49, test 2) a synthetic sequence of amino acids 1–29 of human parathyroid hormone, and test 3) living Nanobacterium cells. The spleens were prepared according to Example 2 by using a sterile technique into RPMI 1640 cell culture medium containing 10% of FCS, 100 IU/ml of penicillin and 100 μg/ml of streptomycin. For hybridoma fusion, myeloma cells and HAT (Gibco) in 1× concentration were further added, and then 10% by volume of the growth factor preparation produced according to Example 1.

The cultures were retained in 96-well plates under conditions 5% of $CO_2$/95% of air, 37° C. The first screenings in the tests were carried out in the following manner: test 1) after 8 days, test 2) after 10 days, and test 3) after 9 days. The second screenings were carried out in the following manner: test 1) after 17 days, test 2) after 19 days, and test 3) after 16 days of culture. The screenings were carried out by an enzyme-linked immunosorbent assay, i.e. ELISA technique, by using said antigens and alkalic phosphatase-coupled anti-mouse antibodies. The optical density of negative controls in A405 was 0.189±0.041 on average. Finally, the number of antigen-positive wells containing hybridomas was checked. The results are shown in Table 1.

TABLE 1

The proportion of positive wells in all the examined wells in mutually independent tests.

| | 1. screening | | | 2. screening | | | Number of antigen-positive wells with hybridomas |
|---|---|---|---|---|---|---|---|
| | Proportion (%) of positive wells | A405 X ± SD | n | Proportion (%) of positive wells | A405 X ± SD | n | |
| test 1 | 95 | 1.20 ± 0.41 | 91 | 90 | 1.51 ± 0.46 | 86 | 28 |
| test 2 | 93 | 1.09 ± 0.32 | 90 | 79 | 1.43 ± 0.51 | 76 | 34 |
| test 3 | 85 | 0.98 ± 0.35 | 82 | 82 | 1.10 ± 0.29 | 77 | 31 |

In the preparation of conventional hybridoma cells to produce monoclonal antibodies in cell cultures, the cell hybrids formed are cultured after the fusion under in vitro conditions in HAT selection pressure, wherein both the unfused myeloma cells and the normal lymphocytes die, and only the hybrids composed of lymphocytes and myeloma cells remain. This process lasts for about two weeks, after which the culture should not contain other living cells. After this stage, desired cell hybrids are selected by means of an antigen for instance by using ELISA. Under normal conditions, the proportion of positive wells varies from below 1% to 30%, depending on the properties of the antigen, the success of the performed cell fusion and the cell division ratio.

In the tests performed in this context, wherein the growth factor preparation was added to the culture after the cell fusion, the unfused B lymphocytes remained viable for several weeks, which is different from the normal situation. The assay of the antibody by using a specific antigen resulted in a proportion of positive wells in all the examined wells of even 95%. The situation did not correlate with the final number of positive hybridomas. This situation endured for several weeks. The optical density in the ELISA results showed that the production of antibodies in wells not containing cell hybrids was significant, since the result corresponded to the results of the so-called actual positive wells, (i.e. wells containing hybridomas producing a specific antibody). In comparison with negative controls, the ELISA result in the wells was at least 2–5 -fold.

The explanation for the situation described above is the occurrence of polyclonal stimulation, which remains under in vitro conditions for several weeks in culturing in the presence of the growth-stimulating growth factor preparation. The growth-stimulating growth factor preparation stimulated B lymphocytes producing an antibody against the antigen concerned in cultures in such a manner that it was possible to detect antibody production by means of ELISA technique even after weeks from the cell fusion. When estimated on the basis of the optical density, the amount of the produced, non-hybridoma-originated antibodies is thus in the same range as that produced by hybridomas.

EXAMPLE 4

The spleen of a mouse immunized with Nanobacteria was prepared, and the cells were released into a cell culture medium RPMI 1640+10% of FCS+100 IU/ml of penicillin and 100 µg/ml of streptomycin at a cell density of $1\times10^7$/ml. This culture was supplemented with 20% by volume of the growth factor preparation produced according to Example 1 at the very beginning of the culture (5% of $CO_2$/95% of air). The culture was microscopically observed for several weeks. Said culture, as distinct from a control lacking said growth factor preparation, remained viable and produced healthy-looking cells, which survived in the culture even for two months, whereafter the culture was frozen in liquid nitrogen. After culture of about one and a half months, a cell sample was taken of the culture, said sample being examined by means of the fluorescence activated cell sampler (FACS) method by using a B lymphocyte marker (Roitt, I., supra). The result was that the culture contained B lymphocytes. The result shows that in vivo activated B lymphocytes can be cultured in cell cultures by means of the described growth factor preparation even for months.

EXAMPLE 5

Human mononuclear cells were separated from 20 ml of peripheral blood from healthy donors with the Ficoll-Paque method by using an aseptic technique according to the instructions provided by the manufacturer (Pharmacia, Uppsala, Sweden). The cells were cultured at a density of about $4\times10^6$/ml for three weeks in HMIX medium containing 30% by volume of the growth factor preparation produced according to Example 1. In tens of control cultures, which contained no said growth factor preparation, no cells survived. However, the cultures of all four test persons, these cultures containing said growth factor preparation, contained an abundant lymphocyte population which remained viable and multiplied. The cells had clustered in large clumps and spread out of the clumps towards the periphery. The cells resembled lymphocytes, and most of them showed positive immunostaining results for human cell surface immunoglobulins. The staining was carried out according to a method described by Roitt (Roitt, I., Essential Immunology, Blackwell Scientific Publications, Oxford, 1994). The cell surface-associated immunoglobulins prove that the cells in the culture are B lymphocytes. These cultures remained viable for at least 7 weeks.

We claim:

1. A plasma cell-stimulating growth factor preparation which stimulates proliferation of antibody-producing B lymphocytes, said preparation consisting of cell culture medium recovered from a mixed thymocyte culture comprising thymocytes originating from different species of mammals.

2. A plasma cell-stimulating growth factor preparation according to claim 1 wherein the species of mammals are mouse and rat.

3. A cell culture medium comprising a plasma cell-stimulating growth factor preparation according to claim 1.

4. A cell culture medium according to claim 3 comprising 1–50% by volume of said plasma cell-stimulating growth factor preparation.

5. A process for production of a cell culture supernatant exhibiting a plasma cell-stimulating growth factor activity which stimulates proliferation of antibody-producing B lymphocytes, comprising the steps of:
   (a) co-culturing thymocytes originating from different species of mammals in a cell culture with a cell culture medium; and
   (b) recovering said cell culture medium from said cell culture, thereby producing said cell culture supernatant.

6. A process according to claim 5, wherein said thymocytes are obtained from the thymuses of animals of two different species of mammals by aseptically removing the thymuses, releasing the thymocytes and washing them, whereafter said thymocytes are suspended in said cell culture medium and cultured together.

7. A process for culturing plasma cells comprising a step of culturing said plasma cells in a cell culture medium according to claim 3.

8. A process according to claim 7, wherein said plasma cells are murine or human plasma cells.

9. A process for producing an antibody comprising the steps of: (a) culturing antibody-producing cells in a cell culture medium according to claim 3, and (b) recovering an antibody produced by said antibody-producing cells.

10. A process according to claim 9, wherein said antibody-producing cells are plasma cells which produce polyclonal antibodies.

11. A process according to claim 9, wherein said antibody-producing cells are plasma cells from one plasma cell clone and said plasma cell clone produces a monospecific antibody.

12. A process according to claim 9 wherein said antibody-producing cells are hybridoma cells from one hybridoma cell clone and said hybridoma cell clone produces a monoclonal antibody.

* * * * *

UNITED STATES PATENT AND TRADEMARK OFFICE
CERTIFICATE OF CORRECTION

PATENT NO. : 5,776,778
DATED : July 7, 1998
INVENTOR(S) : KAJANDER et al.

It is certified that error appears in the above-identified patent and that said Letters Patent is hereby corrected as shown below:

ON THE COVER PAGE:

Please add:

-- Related U.S. Application Data

[63] Continuation of international application number PCT/FI95/00335, file June 9, 1995 --

Signed and Sealed this

Twentieth Day of April, 1999

*Attest:*

Q. TODD DICKINSON

*Attesting Officer*    *Acting Commissioner of Patents and Trademarks*